United States Patent
Antonelli et al.

(10) Patent No.: US 6,235,297 B1
(45) Date of Patent: May 22, 2001

(54) METHODS FOR TREATING SKIN WITH 3-HYDROXY BENZOIC ACID AND RELATED COMPOSITIONS

(75) Inventors: Eric Nicholas Antonelli, Long Branch, NJ (US); George Harvey Armstrong, New Kinsington, PA (US); Reilly Canay Dulog, Edison; James Joseph Ferone, Bridgewater, both of NJ (US); Alexander Lukacs, III, Wayne, PA (US); Frank Charles Pagano, Avenell, NJ (US); David Allen Porter, Phillipsburg, NJ (US); Gale McElroy Reinhart, Middletown, NJ (US); Beverly Ann Reisinger, East Brunswick, NJ (US)

(73) Assignee: Revlon Consumer Products Corporation, New York, NY (US)

( * ) Notice: Subject to any disclaimer, the term of this patent is extended or adjusted under 35 U.S.C. 154(b) by 0 days.

(21) Appl. No.: 09/326,932

(22) Filed: Jun. 7, 1999

(51) Int. Cl.[7] ................................ A61K 7/00; A61K 7/44
(52) U.S. Cl. .............................................. 424/401; 424/60
(58) Field of Search ........................................ 424/401, 60

(56) References Cited

U.S. PATENT DOCUMENTS

| 5,573,759 | * | 11/1996 | Blank | 424/60 |
|---|---|---|---|---|
| 5,691,327 | | 11/1997 | Blank | 514/159 |
| 5,766,613 | * | 6/1998 | Arraudeau et al. | 424/401 |
| 5,885,595 | * | 3/1999 | Corey et al. | 424/401 |
| 5,891,451 | | 4/1999 | Guerrero | 424/401 |

FOREIGN PATENT DOCUMENTS

9503781 * 2/1995 (WO).

* cited by examiner

Primary Examiner—James M. Spear
Assistant Examiner—Blessing Fubara
(74) Attorney, Agent, or Firm—Julie Blackburn

(57) ABSTRACT

A method for improving and/or treating one or more conditions of the skin selected from the group consisting of texture, luminosity, radiance, fine lines, wrinkles, skin pigmentation irregularities, sallowness, and photodamage comprising applying to the skin a cosmetic composition comprising 0.01–30% by weight of the total composition of 3-hydroxybenzoic acid and the compositions used therefor.

20 Claims, No Drawings

METHODS FOR TREATING SKIN WITH 3-HYDROXY BENZOIC ACID AND RELATED COMPOSITIONS

TECHNICAL FIELD

The invention is in the field of methods for treating skin for improvement and the related compositions.

BACKGROUND OF THE INVENTION

It is known that alpha and beta hydroxy acids exert beneficial effects on the skin over and above their traditional use to treat *acne vulgaris*. It is generally believed that the beneficial effects attributed to hydroxy acids are due to their mildly acidic nature, which causes gentle exfoliation of the skin to improve skin clarity, color, and tone, and reduce the appearance of wrinkles and fine lines. Certain sensitive individuals find that hydroxy acids cause skin irritation and dryness. Often, such individuals can overcome the sensitivity to one hydroxy acid by switching to another hydroxy acid. In general, the acidity of a hydroxy acid will depend upon the placement of the hydroxyl and carboxylic acid groups. For example, in glycolic acid the hydroxyl group is found on the alpha carbon atom. In salicylic acid, the hydroxyl group is found on the beta, or number 2, carbon atom. Thus glycolic acid tends to be more acidic (hence more irritating) then salicylic acid because the hydroxyl and carboxylic acid groups are closer to each other on the molecule. In addition, the acidity of a hydroxy compound also tends to depend on the number of hydroxyl groups present, i.e. a compound with more hydroxyl groups tends to be more acidic. Ideally, a hydroxy acid will provide mild exfoliation and other beneficial effects to the skin, without causing skin drynesss and irritation.

U.S. Pat. No. 5,573,759 teaches a method for reducing wrinkles and skin atrophy by applying salicylic acid (2-hydroxybenzoic acid) to the skin. The '759 patent teaches that chronic application of salicylic acid-containing compositions to the skin will reduce skin wrinkling and delay the development of new wrinkles. However, because the hydroxyl group of salicylic acid is on the number 2 carbon atom, salicylic acid tends to be more, rather than less, acidic in nature, and irritating for certain individuals with sensitive skin.

U.S. Pat. No. 5,766,613 teaches the use of dihydroxybenzoic acid derivatives to stimulate the process of epidermal renewal in the skin and combat wrinkles, fine lines, blemishes, and acne. The preferred compound is 2,5-dihydroxybenzoic acid. The dihydroxy benzoic acids taught in the '613 patent are even more irritating to skin than salicylic acid because the have an additional hydroxyl group on the gamma carbon atom in addition to the hydroxyl group on the beta carbon atom.

The object of this invention is to provide a method for exfoliating skin and providing beneficial effects such as reducing the appearance of wrinkles and fine lines, and improving skin color, texture, and tone without the undesired effects of skin dryness and irritation.

The object of the invention is to provide a cosmetic composition that improves skin texture, color, clarity, and tone.

SUMMARY OF THE INVENTION

The invention comprises a method for improving and/or treating one or more conditions of the skin selected from the group consisting of texture, luminosity, radiance, fine lines, wrinkles, skin pigmentation irregularities, sallowness, and photodamage comprising applying to the skin a cosmetic composition comprising 0.01–30% by weight of the total composition of 3-hydroxybenzoic acid.

The invention also comprises a cosmetic composition for improving and/or treating skin comprising 0.01–30% by weight of the total composition of 3-hydroxy benzoic acid, in a cosmetically acceptable carrier.

DETAILED DESCRIPTION

I. The Method

In the method of the invention, cosmetic compositions containing 0.01–30%, preferably 0.1–20%, more preferably 0.5–10% by weight of the total composition of 3-hydroxybenzoic acid are applied topically to the skin. The frequency of application will vary, but preferably the composition is applied daily, more preferably from one to four times per day in various forms such as makeup, skin creams and lotions, and sticks such as lipstick. Repeated application of the compositions to skin will provide benefits such as improved skin texture, luminosity, and radiance, and will diminish the appearance of fine lines, wrinkles, skin pigmentation irregularities, sallowness, and photodamage. In general, the longer the use of such compositions, the greater the improvement. Because 3-hydroxy benzoic acid is a gamma hydroxy acid, the undesireable effects sometimes associated with hydroxy acids, such as dryness and skin irritation are minimized.

II. The Composition

The invention also comprises a cosmetic composition for improving and/or treating skin comprising 0.01–30%, preferably 0.1–20%, more preferably 0.5–10% by weight of the total composition of 3-hydroxy benzoic acid, in a cosmetically acceptable carrier. A wide variety of cosmetically acceptable carriers are suitable, including but not limited to, water and oil emulsion lotions, creams, or foundation makeups, anhydrous compositions such as makeup, powder, blush, lipstick, concealer sticks, and the like.

A. Water and Oil Emulsions

The cosmetically acceptable carrier may comprise either water-in-oil or oil-in-water emulsions, which generally comprise about 0.1–99%, preferably 0.5–90%, more preferably 1–85% water; and 0.1–99%, preferably 0.5–90%, more preferably 1–85% oil, all percentages being percentages by weight.

1. Skin Care Emulsions

The water and oil emulsions may be used to prepare skin care compositions, i.e. moisturizing creams or lotions which are applied to skin to moisturize and condition the skin prior to application of foundation. Typically skin care emulsions will contain ingredients which enhance the aesthetics of the formula, such as thickeners, nonionic surfactants, sunscreens, sunblocks, oils, preservatives, and antioxidants.

a. Oils

A variety of oils may be used in the emulsion compositions including silicone oils, fluorinated silicone oils, organic oils from the animal, vegetable, mineral, classes, as well as fluorinated derivatives thereof. Preferably the skin care emulsions of the invention contain silicone oils. More preferably they are also free of animal, vegetable, or mineral oils.

Suitable oils or solvents may be volatile or nonvolatile. The term "volatile" means that the oil has a measureable vapor pressure, or a vapor pressure of at least 2 mm. of mercury at 20° C. The term "nonvolatile" means that the oil has a vapor pressure of less than 2 mm. of mercury at 20° C. Suitable volatile solvents generally have a viscosity of 0.5 to 10 centistokes at 25° C. and include linear silicones, cyclic silicones, paraffinic hydrocarbons, or mixtures thereof.

Cyclic silicones (or cyclomethicones) are of the general formula:

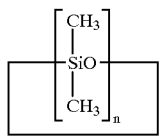

where n=3–7.

Linear volatile silicones in accordance with the invention have the general formula:

$$(CH_3)_3Si-O-[Si(CH_3)_2-O]_n-Si(CH_3)_3$$

where n=0–6, preferably 0–5.

Linear and cyclic volatile silicones are available from various commercial sources including Dow Corning Corporation and General Electric. The Dow Corning volatile silicones are sold under the tradenames Dow Corning 244, 245, 344, and 200 fluids. These fluids comprise octamethylcyclotetrasiloxane, decamethylcyclopentasiloxane, hexamethyldisiloxane, and mixtures thereof.

Also suitable as the volatile oils are various straight or branched chain paraffinic hydrocarbons having 5 to 40 carbon atoms, more preferably 8–20 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference. Preferred volatile paraffinic hydrocarbons have a molecular weight of 70–225, preferably 160 to 190 and a boiling point range of 30 to 320, preferably 60–260 degrees C., and a viscosity of less than 10 cs. at 25 degrees C. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Another $C_{12}$ isoparaffin (isododecane) is distributed by Presperse under the tradename Permethyl 99A. Various $C_{16}$ isoparaffins commercially available, such as isohexadecane (having the tradename Permethyl R), are also suitable.

Nonvolatile silicones, preferably water insoluble, are also suitable for use as the oil component. Such silicones preferably have a viscosity of 10 to 600,000 centistokes, preferably 20 to 100,000 centistokes at 25° C. Suitable water insoluble silicones include dimethicone, methicone, phenyl dimethicone, phenyl trimethicone, simethicone, dimethylhydrogensiloxane, and mixtures thereof. Preferred for use in the invention are low viscosity nonvolatile dimethicones, i.e. dimethicones having a viscosity of 10–25 centipoise at 25° C., either alone or in combination with a cyclomethicone. The combination of cyclomethicone and low viscosity nonvolatile dimethicone provides a light, non-greasy feel to the skin care emulsion.

Other nonvolatile oils are also suitable for use in the cosmetic compositions of the invention. Such oils generally have a viscosity of greater than 10 centipoise at 25° C., and may range in viscosity up to 1,000,000 centipoise at 25° C., and are liquids at room temperature. Examples of nonvolatile oils suitable for use in the compositions of the invention include esters of the formula RCO—OR' wherein R and R' are each independently a $C_{1-25}$, preferably a $C_{4-20}$ straight or branched chain alkyl, alkenyl or alkoxycarbonylalkyl or alkylcarbonyloxyalkyl. Examples of such esters include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, cocodicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, and fatty alcohols such as oleyl alcohol, isocetyl alcohol, and the like, as well as the esters disclosed on pages 24–26 of the *C.T.F.A Cosmetic Ingredient Handbook*, First Edition, 1988, which is hereby incorporated by reference.

The oil may also comprise naturally occuring glyceryl esters of fatty acids, or triglycerides. Both vegetable and animal sources may be used. Examples of such oils include castor oil, lanolin oil, triisocetyl citrate, $C_{10-18}$ triglycerides, caprylic/capric/triglycerides, coconut oil, corn oil, cottonseed oil, linseed oil, mink oil, olive oil, palm oil, illipe butter, rapeseed oil, soybean oil, sunflower seed oil, walnut oil, and the like.

Also suitable as the oil are synthetic or semi-synthetic glyceryl esters, e.g. fatty acid mono-, di-, and triglycerides which are natural fats or oils that have been modified, for example, acetylated castor oil, glyceryl stearate, glyceryl dioleate, glyceryl distearate, glyceryl trioctanoate, glyceryl distearate, glyceryl linoleate, glyceryl myristate, glyceryl isostearate, PEG castor oils, PEG glyceryl oleates, PEG glyceryl stearates, PEG glyceryl tallowates, and so on.

Also suitable as the oil are nonvolatile hydrocarbons such as isoparaffins, hydrogenated polyisobutene, mineral oil, squalene, petrolatum, and so on.

Also suitable as the oil are various lanolin derivatives such as acetylated lanolin, acetylated lanolin alcohol, and so on.

Also suitable as the nonvolatile oil are various fluorinated oils such as fluorinated silicones, fluorinated esters, or perfluoropolyethers. Particularly suitable are fluorosilicones such as trimethylsilyl endcapped fluorosilicone oil, polytrifluoropropylmethylsiloxanes, and similar silicones such as those disclosed in U.S. Pat. No. 5,118,496 which is hereby incorporated by reference. Perfluoropolyethers like those disclosed in U.S. Pat. Nos. 5,183,589, 4,803,067, 5,183,588 all of which are hereby incorporated by reference, which are commercially available from Montefluos under the trademark Fomblin, are also suitable shine enhancers.

Guerbet esters are also suitable oils. The term "guerbet ester" means an ester which is formed by the reaction of a guerbet alcohol having the general formula:

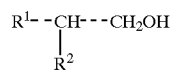

with a carboxylic acid having the general formula:

or

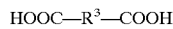

wherein $R^1$ and $R^2$ are each independently a $C_{4-20}$ alkyl and $R^3$ is a substituted or unsubstituted fatty radical such as a $C_{1-50}$ straight or branched chain saturated or unsaturated alkyl or alkylene, or phenyl, wherein the substituents are halogen, hydroxyl, carboxyl, and alkylcarbonylhydroxy. Particularly preferred is a carboxylic acid wherein the R group is such to provide an ingredient known as meadowfoam seed oil.

Suitable guerbet esters are fluoro-guerbet esters formed by the reaction of a guerbet alcohol and carboxylic acid (as defined above), and a fluoroalcohol having the following general formula:

$$CF_3-(CH_2)_n-CH_2-CH_2-OH$$

wherein n is from 3 to 40.

Examples of suitable fluoro guerbet esters are set forth in U.S. Pat. No. 5,488,121 which is hereby incorporated by reference. Suitable fluoro-guerbet esters are also set forth in U.S. Pat. No. 5,312,968 which is hereby incorporated by reference. Most preferred is a guerbet ester having the tentative CTFA name fluoro-octyldodecyl meadowfoamate. This ester is sold by Siltech, Norcross Ga. as Developmental Ester L61125A, under the tradename Silube GME-F.

b. Nonionic Surfactants

Preferably, the skin care emulsions comprise 0.01–25%, preferably 0.1–20%, more preferably 0.5–15% of a nonionic surfactant. The nonionic surfactants may be silicone or organic surfactants. Suitable silicone surfactants are polymeric organosiloxane emulsifiers or surfactants which contain at least one lipophilic radical or portion and at least one hydrophilic radical or portion. The silicone surfactant used in the compositions of the invention may be liquid or solid at room temperature. The surfactant is generally a water-in-oil or oil-in-water type nonionic surfactant, having an Hydrophile/Lipophile Balance (HLB) of 2 to 18, preferably 2 to 12. The HLB of a nonionic surfactant is the balance between the hydrophilic and lipophilic portions of the surfactant and is calculated according to the following formula:

$$HLB+11.7 \times \log M_w/M_o$$

where $M_w$ is the molecular weight of the hydrophilic group portion and $M_o$ is the molecular weight of the lipophilic group portion.

The surfactant generally contains a polymeric backbone including repeating siloxy units that may have cylic, linear or branched repeating units, e.g. di(lower)alkylsiloxy units, preferably dimethylsiloxy units. The hydrophilic portion of the organosiloxane is generally achieved by substitution onto the polymeric backbone of a radical that confers hydrophilic properties to a portion of the molecule. The hydrophilic radical may be substituted on a terminus of the polymeric organosiloxane, or on any one or more repeating units of the polymer. In general, the repeating dimethylsiloxy units of modified polydimethylsiloxane emulsifiers are lipophilic in nature due to the methyl groups, and confer lipophilicity to the molecule. In addition, longer chain alkyl radicals, hydroxy-polypropyleneoxy radicals, or other types of lipophilic radicals may be substituted onto the siloxy backbone to confer further lipophilicity and organocompatibility. If the lipophilic portion of the molecule is due in whole or part to a specific radical, this lipophilic radical may be substituted on a terminus of the organosilicone polymer, or on any one or more repeating units of the polymer. It should also be understood that the silicone surfactant used in the compositions should have at least one hydrophilic portion and one lipophilic portion.

The term "hydrophilic radical" means a radical that, when substituted onto the organosiloxane polymer backbone, confers hydrophilic properties to the substituted portion of the polymer. Examples of radicals that will confer hydrophilicity are hydroxy-polyethyleneoxy, hydroxyl, carboxylates, sulfonates, sulfates, phosphates, or amines.

The term "lipophilic radical" means an organic radical that, when substituted onto the organosiloxane polymer backbone, confers lipophilic properties to the substituted portion of the polymer. Examples of organic radicals which will conver lipophilicity are $C_{1-40}$ straight or branched chain alkyl, fluoro, aryl, aryloxy, $C_{1-40}$ hydrocarbyl acyl, hydroxy-polypropyleneoxy, or mixtures thereof. The $C_{1-40}$ alkyl may be non-interrupted, or interruped by one or more oxygen atoms, a benzene ring, amides, esters, or other functional groups.

The polymeric organosiloxane emulsifier used in the invention may have any of the following general formulas:

$$M_xQ_y,$$

or $$M_xT_y,$$

or $$MD_xD'_yD''_zM$$

wherein each M is independently a substituted or unsubstituted trimethylsiloxy endcap unit. If substituted, one or more of the hydrogens on the endcap methyl groups are substituted, or one or more methyl groups are substituted with a substituent that is a lipophilic radical, a hydrophilic radical, or mixtures thereof. T is a trifunctional siloxy unit having the empirical formula $RR'SiO_{1.5}$ or $RRSiO_{1.5}$. Q is a quadrifunctional siloxy unit having the empirical formula $SiO_2$, and D, D', D", x, y, and z are as set forth below, with the proviso that the compound contains at least one hydrophilic radical and at least one lipophilic radical. Examples of emulsifiers used in the compositions of the invention are of the general formula:

$$MD_xD'_yD''_zM$$

wherein the trimethylsiloxy endcap unit is unsubstituted or mono-substituted, wherein one methyl group is substituted with a lipophilic radical or a hydrophilic radical. Examples of such substituted trimethylsiloxy endcap units include $(CH_3)_2HPSiO$, $(CH_3)_2LPSiO$, $(CH_3)_2CH_2HPSiO$, $(CH_3)_2CH_2LPSiO$, wherein HP is a hydrophilic radical and LP is a lipophilic radical. D, D', and D" are difunctional siloxy units substituted with methyl, hydrogen, a lipophilic radical, a hydrophilic radical or mixtures thereof. In this general formula:

x=0–5000, preferably 1–1000 y=0–5000, preferably 1–1000, and z=0–5000, preferably 0–1000, with the proviso that the compound contains at least one lipophilic radical and at least one hydrophilic radical. Examples of suitable polymers are disclosed in U.S. Pat. No. 4,698,178, which is hereby incorporated by reference.

Particularly preferred are linear silicones of the formula:

$$MD_xD'_yD''_zM$$

wherein

M=RRR' $SiO_{1/2}$ or $RRRSiO_{1/2}$

D=$RRSiO_{2/2}$

D' and D"=$RR'SiO_{2/2}$; and x, y, and z are each independently 0–1000, where R is methyl or hydrogen, and R' is a hydrophilic radical.

Most preferred is wherein

M=trimethylsiloxy or hydroxy-substituted trimethylsiloxy,

D=Si[(CH$_3$)][(CH$_2$)$_n$CH$_3$]O$_{2/2}$ where n=1–40,

D'=Si [(CH$_3$)][(CH$_2$)$_o$—O—PE)]O$_{2/2}$ where PE is (—C$_2$H$_4$O)$_a$(—C$_3$H$_6$O)$_b$H, o=0–40, a=1–100 and b=1–100, and D"=Si (CH$_3$)$_2$O$_{2/2}$ Typical examples of preferred organosiloxane emulsifiers in accordance with the invention include those set forth below:

I
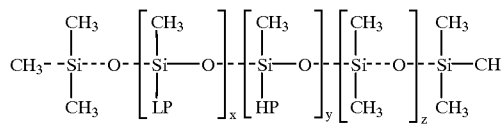

II
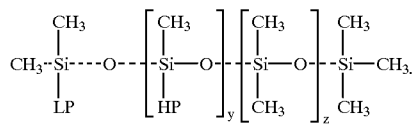

III
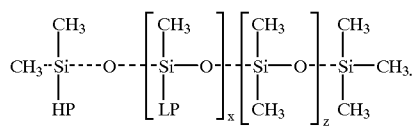

IV
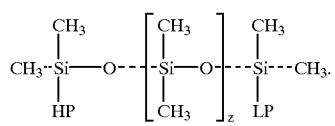

V
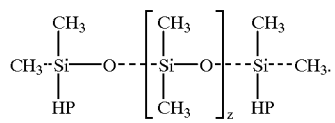

VI
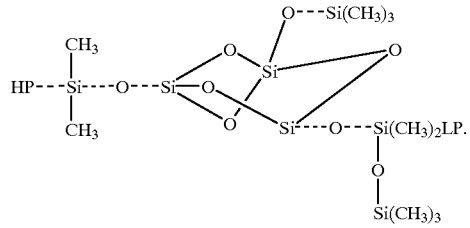

wherein LP is a lipophilic radical

HP is a hydrophilic radical x is 0–5000 y is 0–5000, and z is 0–5000, with the proviso that the organosiloxane contains at least on hydrophilic radical and at least one lipophilic radical.

Preferred are compounds of the generic formula V wherein HP is hydroxyl and the compound is dimethiconol.

Also preferred are compounds of the generic formula I wherein LP is a lipophilic radical containing hydroxy-polypropyleneoxy, HP is a hydrophilic radical containing hydroxy-polyethyleneoxy, and z is at least 1 also referred to as dimethicone copolyol. Preferred is a compound of the formula:

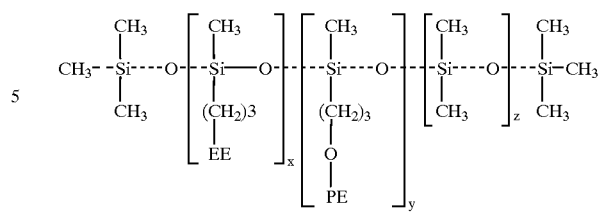

PE is (—C$_2$H$_4$O)$_a$(—C$_3$H$_6$O)$_b$—H and

EE is (—CH$_2$H$_4$O)$_a$—H wherein x, y, and z are as described herein.

Silicone surfactants useful in the compositions are sold by Dow Corning, as well as Union Carbide under the Silwet™ tradename.

Examples of organic nonionic surfactants include alkoxylated alcohols, formed by the reaction of an alcohol with an alkylene oxide, usually ethylene or propylene oxide. Preferably the alcohol is a fatty alcohol having 6 to 30 carbon atoms, and a straight or branched, saturated or unsaturated carbon chain. Examples of such ingredients include Steareth-2 to 100 which is formed by the reaction of stearyl alcohol with ethylene oxide where the number of repeating ethylene oxide units ranges from 2 to 100. Also suitable are Beheneth 5 to 30, Ceteareth 2–100, formed by the reaction of a mixture of cetyl and stearyl alcohol with ethylene oxide, where the number of repeating ethylene oxide units in the molecule is 2 to 100; Ceteth 1–45 which is formed by the reaction of cetyl alcohol and ethylene oxide, and the number of repeating ethylene oxide units is 1 to 45, and so on. Particularly preferred is Steareth 2–100, more particularly a combination of Steareth-2 and Steareth-21 in a ratio of about 1 part Steareth-2 to about 2 parts Steareth-21.

Also suitable as the nonionic surfactant are alkyoxylated carboxylic acids, which are formed by the reaction of a carboxylic acid with an alkylene oxide or with a polymeric ether. The resulting products have the general formula:

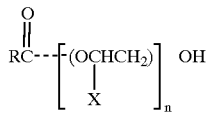

or

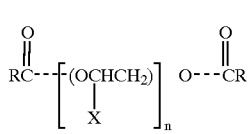

where RCO is the carboxylic ester radical, X is hydrogen or lower alkyl, and n is the number of polymerized alkoxy groups. In the case of the diesters, the two RCO- groups do not need to be identical. Preferably, R is a C$_{6-30}$ straight or branched chain, saturated or unsaturated alkyl, and n is from 1–100.

Other suitable nonionic surfactants include alkoxylated sorbitan and alkoxylated sorbitan derivatives. For example, alkoxylation, in particular, ethoxylation, of sorbitan provides polyalkoxylated sorbitan derivatives. Esterification of polyalkoxylated sorbitan provides sorbitan esters such as the polysorbates. Examples of such ingredients include Polysorbates 20–85, sorbitan oleate, sorbitan palmitate, sorbitan sesquiisostearate, sorbitan stearate, and so on.

c. Sunscreens and Sunblocks

Preferably, the skin care emulsions additionally contain 0.01–30%, more preferably 0.1–20%, most preferably 0.5–15% by weight of the total composition of sunscreens, sunblocks, or a combination thereof.

A sunscreen is defined as an ingredient that absorbs at least 85 percent of the light in the UV range at wavelengths from 290 to 320 nanometers, but transmits UV light at wavelengths longer than 320 nanometers, e.g. chemically reacts upon exposure to UV light. Suitable sunscreens that may be included in the compositions of the invention are set forth on page 582 of the *CTFA Cosmetic Ingredient Handbook*, Second Edition, 1992, as well as U.S. Pat. No. 5,620,965, both of which are hereby incorpated by reference. Examples of such sunscreen materials are p-aminobenzoic acid (PABA), cinoxate, diethanolamine p-methoxycinnamate DEA-methoxycinnamate), Digalloyl trioleate, dioxybenzone (Benzophenone-8), ethyl 4-[bis-(hydroxypropyl)] aminobenzoate (ethyl dihydroxypropyl PABA), 2-ethylhexyl-2-cyano-3,3-diphenylacrylate (octocrylene), ethylhexyl p-methoxycinnamate (Octyl methoxycinnamate), 2-ethylhexyl salicylate (Octyl salicylate), glyceryl aminobenzoate (Glyceryl PABA), homosalate, lawsone with dihydroxyacetone, menthyl anthranilate, oxybenzone (Benzophenone-3), Padimate A (Pentyl Dimethyl PABA), Padimate O, (Octyl Dimethyl PABA), 2-Phenylbenzimidazole-5-sulfonic acid (Phenylbenzimidazole Sulfonic acid), Red Petrolatum, Sulisobenzone (Benzophenone-4), triethanolamine salicylate (TEA-Salicylates), and so on.

Sunblocks are generally particulate materials, such as zinc oxide or titanium dioxide, which physically block ultraviolet radiation. Such particulates have particle sizes ranging from 0.05 to 100 microns. The emulsion compositions of the invention may contain sunscreens and sunblocks in combination, or may only contain one or the other. Generally, if sunblocks are present, they are incorporated in the same percentage ranges as set forth for the sunscreens, above.

d. Cosolvents

Since 3-hydroxybenzoic acid is not readily soluble in water, it is desireable to utilize one or more co-solvents for the compound in the compositions of the invention. Suggested ranges of co-solvent are 0.01–15%, preferably 0.1–10%, more preferably 0.5–8% by weight of the total composition. Suitable co-solvents are mono-, or dihydric alcohols. Examples of suitable monohydric alcohols are ethanol, isopropanol, butanol, and the like. Examples of dihydric alcohols include butylene glycol, propylene glycol, ethylene glycol, and the like. Suitable ethers include monomeric, homopolymeric and block copolymeric ethers. Such ethers are formed by the polymerization of monomeric alkylene oxides, generally ethylene or propylene oxide. Such polymeric ethers have the following general formula:

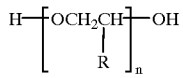

wherein R is H or lower alkyl and n is the number of repeating monomer units, and ranges from 1 to 500. Preferably the co-solvent is a polymeric ether having the above formula wherein R is H and n is 1–20, preferably 6, or one or more dihydric alcohols. Most preferred are PPG-14 butyl ether and PEG-6.

e. Aqueous Thickeners

Preferably, the emulsion compositions contain one or more aqueous thickeners, e.g. water soluble ingredients which are capable of thickening the aqueous portion of the emulsion. Suggested ranges of aqueous thickeners are 0.01–15%, preferably 0.05–10%, more preferably 0.5–8% by weight of the total composition. Examples of aqueous thickeners include gums, hydrophilic colloids, inorganic salts, fatty alcohols, synthetic polymers, and the like. Examples of inorganic salts include silicates, sulfates, pyrophosphates, sulfites, and the like, including magnesium aluminum silicate, aluminum silicate, aluminum sulfate, boron nitride, calcium silicate, calcium pyrophosphate, sodium magnesium silicate, and the like.

Examples of gums and hydrocolloids include xanthan gum, agarose, alginic acid, agar, calcium alginate, carboxymethyl chitin, carboxymethyl cellulose, carboxymethyl dextran, carboxymethyl chitosan, cetyl glycol, dextrin, gellan gum, gelatin, hyaluronic acid, sodium carageenan, hydroxypropyl cellulose, hydroxyethyl cellulose, locust bean gum, karaya gum, maltodextrin, methyl cellulose, and so on.

Examples of synthetic polymer thickeners include polymers comprised of acrylate, methacrylate, and/or acrylic acid monomer units, or sodium derivatives thereof (e.g. wherein the hydrogen on the hydroxyl group of the acrylic acid is replaced by sodium). Examples of polymeric thickeners include acrylates/C10–30 itaconate copolymer, acrylates/steareth-20 methacrylate copolymer, acrylates/vinyl isodeanoate crosspolymer, sodium polyacrylate, sodium polymethacrylate, sodium polyacrylate starch, sodium polystyrene sulfonate, sodium styrene/acrylates copolymer, starch/acrylates/acrylamide copolymer, ammonium acrylates copolymer, acrylamides copolymer, acrylates/acetoacetoxy methacrylate copolymer, acrylates C10–30 alkyl acrylates crosspolymer, acrylates/ceteth-20 itaconate copolymer, acrylates/ceteth-20 methacrylate copolymer, acrylates/steareth-20 methacrylate copolymer, and mixtures thereof.

Preferably, the skin care emulsions contain both an inorganic salt thickener and a gum/hydrocolloid thickener, in a ratio of 1:10 to 10:1 respectively, more preferably in a ratio of about 2 to 1 respectively. Most preferably the inorganic thickener is magnesium aluminum silicate and the gum/hydrocolloid thickener is xanthan gum.

Prefered skin emulsion compositions are oil-in-water emulsions comprising, by weight of the total composition:
- 20–70% water,
- 0.5–10% 3-hydroxybenzoic acid,
- 0.1–15% of a nonionic surfactant selected from the group consisting of a silicone surfactant, an organic surfactant having an HLB of 2–12, and mixtures thereof,
- 0.5–15% of a sunscreen,
- 0.5–8% co-solvent, and
- 0.5–8% aqueous thickener.

B. Foundation Makeup

The water and oil emulsion compositions may also be in the form of foundation makeup compositions, which are applied to the face to cover skin defects, even skin tone, and provide a more flawless-appearing finish to facial skin. Water and oil emulsion foundation makeup compositions in accordance with the invention may generally contain oils, nonionic surfactants, sunscreens or sunblocks, cosolvents, aqueous thickeners, and other ingredients as set forth for the skin care emulsions described above, and in the same general ranges. In addition, the foundation makeup compositions will contain appreciable levels of pigment and/or powder, which will provide the desired color to the face upon application, as well as humectants, pH adjusters, preservatives, antioxidants, and the like.

1. Pigments and Powders

The foundation makeup compositions of the invention may contain 0.1–70%, preferably 0.5–40%, more preferably 1–25% by weight of the total composition, of pigments, powders, or mixtures thereof, having particle sizes of 0.02 to 100, preferably 0.5 to 100, microns. Powders are generally non-colored (for example white), and are generally not used to provide color, but to mute color. Examples of powder-type materials include bismuth oxychloride, titanated mica, fumed silica, spherical silica, nylon-12, polymethylmethacrylate particles, polyethylene particles, polypropylene particles, micronized teflon, boron nitride, aluminum starch octenylsuccinate, bentonite, chalk, kaolin, talc, mica, alumina, silk powder, sericite, soy flour, tin oxide, walnut shell powder, or mixtures thereof. The above mentioned powders may be surface treated with lecithin, amino acids, mineral oil, silicone oil or various other agents either alone or in combination, which coat the powder surface and render the particles more lipophilic in nature.

Various organic and inorganic pigments are used in the foundation compositions to provide color. The organic pigments are generally various aromatic types including azo, indigoid, triphenylmethane, anthraquinone, and xanthine dyes which are designated as D&C and FD&C blues, browns, greens, oranges, reds, yellows, etc. Organic pigments generally consist of insoluble metallic salts of certified color additives, referred to as the Lakes, in particular the Lakes of D&C and FD&C colors. Inorganic pigments include iron oxides, ultramarines, chromium, chromium hydroxide colors, and mixtures thereof.

Preferably the foundation makeup composition will contain both powders and pigments. Generally the weight ratio of powders to pigments ranges from 1:50 to 50:1.

It may be desired that the particulates be surface coated or surface treated with materials which provide hydrophobicity to the particle surface. Examples of such coatings include silicones, lecithin, perfluoropolymethyl isopropyl ether, fluorinated silicones, lecithin, and the like. Particularly preferred are silicone treated pigments as disclosed in U.S. Pat. No. 5,143,722, as well as pigments which are coated with perfluoropolymethyl isopropyl ether.

2. Humectants

It may be desireable to include one or more humectants in the foundation makeup compositions of the invention. If so, a range of 0.1–15%, preferably 0.1–10%, more preferably 0.5–8% by weight of the total composition is suggested. Suitable humectants are polyhydric alcohols such as glycerin, inositol, 1,2,6-hexanetriol, mannitol, sorbitol, urea, xylitol, and mixtures thereof. Preferably, the makeup composition contains glycerin.

Preferred foundation makeup compositions in accordance with the invention are water-in-oil emulsions comprising, by weight of the total composition:
- 30–80% water,
- 0.5–10% 3-hydroxybenzoic acid
- 1–30% of an oil selected from the group consisting of volatile silicone, nonvolatile silicone and mixtures thereof,
- 0.1–10% of a silicone surfactant, a nonionic organic surfactant having an HLB of 2–12, and mixtures thereof,
- 0.5–8% co-solvent,
- 0.5–8% aqueous thickener, and
- 0.1–30% of a pigment, powder, or mixtures thereof.

Additionally the compositions comprise 0.5–8% by weight of the total composition of humectant.

B. Anhydrous Compositions

The cosmetically acceptable carrier may be in the form of an anhydrous solid, semi-solid, or liquid, such as blush, lipstick, foundation makeup in the cake, cream, or stick form, concealer, eyeshadow and the like.

1. Anhydrous Foundation Makeup

The cosmetically acceptable carrier may be a substantially anhydrous foundation makeup in the stick, cake, or cream form. The term "substantially anhydrous" means that no water is added, although trace amounts of water may exist in some of the ingredients used in the composition. Generally, such makeup compositions comprise all of the ingredients mentioned herein with respect to emulsion compositions, and in the same general ranges, except for the absence of water. In addition, such anhydrous compositions will desireable contain one or more structuring agents which cause the composition to maintain structure and shape.

Preferred anhydrous foundation compositions comprise, by weight of the total composition:
- 0.5–10% 3-hydroxybenzoic acid
- 1–70% of an oil selected from the group consisting of volatile silicone, nonvolatile silicone, esters of the formula RCO—OR' wherein R and R' are as defined above, glyceryl esters of fatty acids,
- 0.1–10% of a nonionic silicone or organic surfactant having an HLB of 2–12, and
- 0.1–70% of a pigment, powder, or mixtures thereof; and
- 1–50% structuring agent.

The oils, pigments, powders, and non-ionic surfactants that may be used in the anhydrous makeup compositions are the same as those mentioned herein with respect to the emulsion compositions.

a. Structuring Agents

Preferably, the anhydrous compositions contain 1–60%, more preferably 2–50%, most preferably 5–45% by weight of the total composition of a structuring agent. The structuring agent is a solid or semi-solid at 25° C., and is capable of providing structure to the composition such that, if desired, it maintains its shape when poured into a stick mold or compact case. Preferably, structuring agents are waxes, either silicone waxes or animal, vegetable, or mineral waxes. Examples of suitable silicone waxes include stearyl dimethicone, behenoxy dimethicone, and silicone ester waxes such as those disclosed in U.S. Pat. No. 5,725,845, which is hereby incorporated by reference. Other animal, vegetable, and mineral waxes that are suitable structuring agents include apple, avocado, bayberry, beeswax, candelilla, carnauba, ceresin, hydrogenated jojoba oil, hydrogenated jojoba wax, hydrogenated microcrystalline wax, hydrogenated rice bran wax, jojoba wax, lanolin wax, microcrystalline wax, mink wax, montan wax, orange wax, ouricury wax, oxidized beeswax, ozokerite, palm kernel wax, paraffin, PEG-beeswax, rice wax, shellac wax, spent grain wax, synthetic wax, and mixtures thereof.

2. Lipstick

Suitable lipstick compositions generally comprise, by weight of the total composition:
- 0.1–30% 3-hydroxybenzoic acid,
- 1–65% oil, and
- 1–50% structuring agent.

Suitable oils and structuring agents are as mentioned above with respect to the skin care emulsions and anhydrous compositions.

The 3-hydroxybenzoic acid may be used alone in the compositions or it may be complexed with one or more complexing agents such as hydrolyzed animal or vegetable protein, polymers and the like, as described in U.S. Pat. No. 5,449,519, which is hereby incorporated by reference.

The invention will be further described in connection with the following examples, which are set forth for the purposes of illustration only.

EXAMPLE 1

Skin care compositions were prepared as follows:

|  | w/w % | | |
| --- | --- | --- | --- |
|  | 1 | 2 | 3 |
| Water | 29.55 | 29.55 | 31.55 |
| Disodium EDTA | 0.20 | 0.20 | 0.20 |
| Methylparaben | 0.20 | 0.20 | 0.20 |
| Ethylparaben | 0.15 | 0.15 | 0.15 |
| Butylene glycol | 5.00 | 5.00 | 5.00 |
| Glycerin | 3.00 | 3.00 | 3.00 |
| Magnesium aluminum silicate solution (6%) | 12.50 | 12.50 | 12.50 |
| Xanthan gum solution (3%) | 16.60 | 16.60 | 16.60 |
| Cetyl alcohol | 0.20 | 0.20 | 0.20 |
| Lecithin | 0.10 | 0.10 | 0.10 |
| Steareth-2 | 2.50 | 2.50 | 2.50 |
| Steareth-21 | 2.40 | 2.40 | 2.40 |
| Propylene glycol dicaprylate/dicaprate | 1.00 | 1.00 | 1.00 |
| PPG-15 stearyl ether | 24.00 | 24.00 | 24.00 |
| 3-hydroxybenzoic acid | 2.00 | — | — |
| Salicylic acid | — | 2.00 | — |
| Imidazolidinyl urea | 0.30 | 0.30 | 0.30 |
| Fragrance | 0.20 | 0.20 | 0.20 |
| Propyl paraben | 0.10 | 0.10 | 0.10 |

The compositions were made by combining the ingredients and mixing well to form an oil in water emulsion. Formula 1 had a pH of 3.55. Formula 2 had a pH of 2.75, and Formula 3, the control, had a pH of 4.86

EXAMPLE 2

A 12 week double blind photoaging study was conducted with Formulas 1–3, above with 68 female subjects approximately 35 to 60 years in age having slight to moderate photodamage. The subjects were divided into three groups. Formula 1 from Example 1 was applied to 23 subjects ("Group One"). Formula 2 was applied to 24 subjects ("Group Two") and Formula 3 was applied to 23 subjects ("Group Three"). The compositions were applied by the subjects in the morning and in the evening, shortly before going to bed. Subjects were instructed to return to the study center for evaluation at 2, 4, 8, and 12 weeks. At 2, 4, 8, and 12 weeks, subjects were asked to complete a self-assessment questionnaire. At baseline and at 12 weeks, a dermatologist evaluated the subjects and graded their faces for a series of dermatological attributes as set forth below by noting the percentage of subjects that exhibited improvement from baseline for the characteristic given:

| Formula | 1 | 2 | 3 |
| --- | --- | --- | --- |
| Texture | 100 | 83 | 91 |
| Clarity | 78 | 79 | 83 |
| Fine wrinkling | 70 | 46 | 57 |
| Discrete pigmentation | 67 | 63 | 65 |
| Mottled pigmentation | 87 | 71 | 61 |
| Sallowness | 70 | 46 | 61 |
| Clogged pores | 61 | 75 | 35 |
| Overall photodamage | 65 | 58 | 43 |

-continued

| Formula | 1 | 2 | 3 |
| --- | --- | --- | --- |
| Crinkling/sagging | 26 | 29 | 22 |
| Laxity | 4 | 4 | 0 |
| Coarse wrinkling | 0 | 13 | 4 |

The above illustrates that Formula 1, containing 3 hydroxybenzoic acid, showed improved results over Formulas 2 and 3 with respect to texture, fine wrinkling, discrete pigmentation, mottled pigmentation, sallowness, and overall photodamage when rated by dermatologists.

Subjects who participated in the study were also asked to grade the performance of the compositions for various attributes based upon their perceptions (as opposed to the perceptions of a dermatologist). The scores for subject's self assessments at two and twelve weeks are as follows. The numbers express the percentage of subjects who agreed:

|  | two weeks | | | twelve weeks | | |
| --- | --- | --- | --- | --- | --- | --- |
| Formula | 1 | 2 | 3 | 1 | 2 | 3 |
| Doesn't leave skin flaky | 88 | 83 | 88 | 81 | 96 | 87 |
| Doesn't leave skin dry | 83 | 88 | 88 | 95 | 92 | 78 |
| Leaves skin feeling smooth | 75 | 96 | 88 | 76 | 83 | 100 |
| Leave skin feeling soft/supple 83 | 88 | 83 | 81 | 75 | 96 | |
| Improves overall feel | 67 | 88 | 79 | 67 | 83 | 83 |
| Skin appears smoother | 75 | 79 | 79 | 67 | 75 | 87 |
| Feels comfortable on skin | 75 | 88 | 67 | 67 | 83 | 83 |
| Skin appears healthier looking | 72 | 75 | 79 | 43 | 75 | 70 |
| Improves skin texture | 67 | 83 | 71 | 67 | 67 | 83 |
| Skin appears fresher | 67 | 79 | 71 | 52 | 63 | 70 |
| Improves overall look of skin | 63 | 63 | 63 | 48 | 46 | 65 |
| Skin feels firmer | 42 | 67 | 71 | 52 | 54 | 61 |
| Skin appears more luminous | 54 | 71 | 58 | 62 | 50 | 57 |
| Skin appears firmer | 42 | 67 | 67 | 52 | 54 | 61 |
| Skin appears more radiant | 58 | 54 | 50 | 52 | 50 | 48 |
| Improves skin clarity | 38 | 58 | 63 | 38 | 58 | 52 |
| Diminishes fine lines and wrinkles | 46 | 63 | 50 | 33 | 42 | 43 |
| Makes pores appear smaller, tighter | 54 | 46 | 46 | 29 | 42 | 52 |
| Skin tones appear more even | 46 | 46 | 46 | 29 | 42 | 43 |
| Skin appears younger looking | 46 | 54 | 42 | 38 | 38 | 39 |
| Makes pore appear less noticeable | 54 | 46 | 42 | 29 | 38 | 43 |
| Firms skin around the eyes | 38 | 46 | 46 | 33 | 50 | 43 |
| Diminishes fine dry lines, wrinkles | 42 | 46 | 38 | 33 | 42 | 43 |
| Reduces visible signs of aging 38 | 46 | 38 | 38 | 46 | 43 | |
| Improves skin tones around the eye | 29 | 42 | 33 | 38 | 38 | 43 |
| Diminishes fine lines, wrinkles-lips | 25 | 33 | 42 | 19 | 38 | 26 |
| Improves skin color | 42 | 29 | 29 | 29 | 2 1 | 26 |
| Lightens appearance of discoloration | 33 | 25 | 25 | 33 | 25 | 30 |
| Diminishes appearance of dark circles | 17 | 21 | 25 | 38 | 25 | 26 |
| Blotchy spots become less noticeable | 25 | 4 | 21 | 24 | 13 | 17 |

It is noted that the scores reported by subjects based upon their own perceptions were less favorable than the scores reported by dermatologists. It is believed that the subjects were reacting negatively to the aesthetics of the cosmetically acceptable carrier, since a substantial number of complaints were received about the formula.

EXAMPLE 4

An oil in water emulsion liquid makeup formula was made as follows:

|  | w/w % |
|---|---|
| 1 Water | QS |
| 1 Magnesium aluminum silicate | 1.2255 |
| 2 Butylene glycol | 3.9216 |
| 3 Ethyl paraben | 0.0980 |
| 3 Methyl paraben | 0.2941 |
| 3 Simethicone | 0.1471 |
| 4 Sodium polymethacrylate | 0.9804 |
| 4 Sorbitan sesquioleate | 0.4902 |
| 4 Glycerin (96% in water) | 4.9020 |
| 5 Trisodium EDTA | 0.1471 |
| 5 Benzoic acid | 0.1961 |
| 6 3-hydroxy benzoic acid | 2.000 |
| 7 Talc | 2.3039 |
| 7 Titanium dioxide | 4.9020 |
| 7 Iron oxide yellow | 0.9314 |
| 7 Iron oxide/talc: 33/67 | 0.9314 |
| 7 Black iron oxide | 0.1961 |
| 8 Xanthan gum | 0.3431 |
| 8 Butylene glycol | 0.9804 |
| 9 Cyclomethicone | 14.7059 |
| 9 Polysorbate 20 | 0.9804 |
| 9 Diisopropyl dimer dilinoleate | 3.4314 |
| 10 Imidazolidinyl urea | 0.2941 |

Sequence 1 was processed in a colloid mill until dispersed. Sequences 2 and 3 were added to Sequence 1 and mixed. Sequences 4, 5, and 7 were then added to the mixture and the composition was milled until the pigment was dispersed. Sequence 8 was then added until uniformly mixed and dispersed throughout the composition. Sequence 6 was added and mixed well. This mixture was heated to a temperature of 68 to 75° C. Separately, Sequence 9 was heated to a temperature of 68 to 75° C. The mixture and Sequence 10 were combined and emulsified for 15 minutes using a high speed sweep mixer. When cooled to room temperature, the resulting liquid makeup composition was poured into glass jars.

EXAMPLE 5

A solid compact makeup was made made as follows:

|  | w/w % |
|---|---|
| 1 Dimethicone | 20.5000 |
| 1 Tridecyl trimellitate | 2.3500 |
| 1 Neopentyl glycol dioctanoate | 5.4000 |
| 1 Sorbitan trioleate | 0.5000 |
| 1 Pentahydrosqualene | 0.5000 |
| 1 Dimethicone/trimethylsiloxy silicate (50:50) | 0.2500 |
| 1 Isopropyl isostearate | 16.1500 |
| 1 Butylated hydroxy anisole | 0.1000 |
| 3 Myristyl myristate | 1.5000 |
| 3 Candelilla wax | 0.7500 |
| 4 Tribehenin | 4.000 |
| 4 Isostearyl behenate | 3.8000 |
| 5 Talc | 4.25 |
| 5 Titanium dioxide | 15.00 |
| 6 Red iron oxide | 0.900 |
| 6 Yellow iron oxide | 3.450 |
| 6 Black iron oxide | 0.300 |
| 7 Nylon 12 | 3.500 |
| 7 Lauroyl lysine | 2.500 |
| 7 Mica | 0.900 |
| 7 Boron nitride | 2.500 |
| 7 Silica | 6.100 |
| 9 Methyl paraben, ethyl paraben, propyl paraben, butyl paraben phenoxyethanol | 1.400 |
| 10 Polyglyceryl-7-isostearate | 1.000 |

-continued

|  | w/w % |
|---|---|
| 10 Laurylmethicone copolyol | 0.500 |
| 5 3-hydroxy benzoic acid | 2.000 |

Sequences 1, 5, 6, and 7 were roller milled three times until homogeneous. Separately, Sequences 3 and 4 were heated to 85° C. The mixture of Sequences 1, 5, 6, and 7 were added to the mixture of Sequences 3 and 4 and the temperature maintained at 85° C. Sequences 9 and 10 were added to the mixture. The composition was cooled. When the temperature reached 75 to 78° C., the composition was poured into containers.

EXAMPLE 5

A lipstick composition was made according to the following formula:

|  | w/w % |
|---|---|
| Synthetic wax | 8.00 |
| Bis-diglyceryl polyacyladipate-2 | 2.00 |
| Triisostearyl citrate | 21.64 |
| Complex* | 20.00 |
| Dimethicone copolyol | 7.00 |
| Vitamin E | 0.10 |
| Aloe | 0.10 |
| Vitamin A palmitate | 0.0001 |
| Vitamin A | 0.0001 |
| Collagen amino acids in water | 0.0001 |
| Methyl paraben | 0.30 |
| Propyl paraben | 0.10 |
| Dimethicone | 1.20 |
| Quaternium 18 hectorite | 0.35 |
| Mica | 5.21 |
| Cyclomethicone | 18.00 |
| Trioctyldodecyl citrate | 10.00 |
| Mica | 5.00 |
| Isostearyl alcohol | 1.00 |
| *Complex |  |
| Acrylates copolymer | 9.00 |
| PEG-20 sorbitan beeswax | 27.00 |
| Cetyl acetate/acetylated lanolin alcohol | 38.70 |
| Lanolin oil | 15.00 |
| Propyl paraben | 0.10 |
| 3-hydroxy benzoic acid | 10.00 |
| Methyl paraben | 0.20 |

The ingredients were combined and mixed well with heat. The molten lipstick composition was poured into molds and allowed to cool.

EXAMPLE 6

A skin treating patch for smoothing lines and wrinkles was made by mixing 98 parts of adhesive with 2 parts 3-hydroxybenzoic acid. This composition was poured onto 50 lb. densified Kraft paper coated with a 3 mil facestock corona treated polyurethane film. The film was run through 60 feet of drying oven. When dry, the film was die cut into appropriate shapes. Immediately prior to use the patch was wet with water and applied to the skin.

While the invention has been described in connection with the preferred embodiment, it is as not intended to limit the scope of the invention to the particular form set forth but, on the contrary, it is intended to cover such alternatives, modifications, and equivalents as may be included within the spirit and scope of the invention as defined by the appended claims.

We claim:

1. A method for improving and/or treating one or more conditions of the skin selected from the group consisting of fine lines, wrinkles, skin pigmentation irregularities, sallowness, and photodamage by applying to the skin a cosmetic composition consisting essentially of 0.01–30% by weight of the total composition of 3-hydroxybenzoic acid.

2. The method of claim 1 wherein the cosmetic composition is a water and oil emulsion skin care composition.

3. The method of claim 2 wherein the cosmetic composition consists essentially of, by weight of the total composition, 1–99% water, and 1–99% oil.

4. The method of claim 3 wherein the oil is selected from the group consisting of:
    (a) volatile silicone,
    (b) nonvolatile silicone, and
    (c) mixtures thereof.

5. The method of claim 4 wherein the volatile silicone is cylcomethicone.

6. The method of claim 4 wherein the non-volatile silicone is dimethicone.

7. The method of claim 4 wherein the composition consists essentially of, 0.1–15% of a sunscreen.

8. The method of claim 7 wherein the composition consists essentially of 0.5–8% of a co-solvent.

9. The method of claim 8 wherein the composition consists essentially of 0.1–15% of a surfactant selected from the group consisting of a nonionic silicone surfactant, a nonionic organic surfactant, and mixtures thereof.

10. The method of claim 9 wherein the composition consists essentially of, by weight of the total composition, 0.5–8% aqueous thickener.

11. A cosmetic composition for improving or treating the skin consisting essentially of, by weight of the total composition, 0.1–30% 3-hydroxybenzoic acid in a cosmetically acceptable carrier.

12. The composition of claim 11 which is a water and oil emulsion consisting essentially of, by weight of the total composition, 0.1–99% water, and 0.1–99% oil.

13. The composition of claim 12 which is a skin care emulsion consisting essentially of:
    20–70% water,
    0.5–10% 3-hydroxybenzoic acid,
    1–30% of an oil selected from the group consisting of volatile silicone, nonvolatile silicone, and mixtures thereof,
    0.1–15% of a nonionic surfactant selected from the group consisting of a silicone surfactant, an organic surfactant having an HLB of 2 to 12, and mixtures thereof,
    0.5–15% of a sunscreen,
    0.5–8% co-solvent, and
    0.5–8% aqueous thickener.

14. The composition of claim 11 which is a foundation makeup consisting essentially of, by weight of the total composition:
    30–80% water,
    0.5–10% 3-hydroxybenzoic acid,
    1–30% of an oil selected from the group consisting of volatile silicone, nonvolatile silicone, and mixtures thereof,
    0.1–10% of a surfactant selected from the group consisting of silicone surfactant, a nonionic organic surfactant having an HLB of 2 to 12, and mixtures thereof,
    0.5–8% co-solvent,
    0.5–8% aqueous thickener, and
    0.1–30% of a pigment, powder, and mixtures thereof.

15. The composition of claim 14 consisting essentially of 0.5–8% humectant.

16. The composition of claim 11 which is an anhydrous foundation makeup consisting essentially of, by weight of the total composition:
    0.1–10% 3-hydroxybenzoic acid,
    1–70% of an oil selected from the group consisting of:
        (a) volatile silicone,
        (b) nonvolatile silicone,
        (c) esters of the formula RCO—OR' where R and R' are each independently a $C_{1-25}$, straight or branched chain alkyl, alkenyl or alkoxycarbonylalkyl or alkylcarbonyloxyalkyl,
        (d) glyceryl esters of fatty acids, and
        (e) mixtures thereof.

17. The composition of claim 16 consisting essentially of 1–60% of a structuring agent.

18. The composition of claim 11 which is a lipstick consisting essentially of, by weight of the total composition:
    0.1–30% 3-hydroxybenzoic acid,
    1–65% oil, and
    1–50% of a structuring agent.

19. A cosmetic lipstick composition for improving or treating the skin or lips comprising, by weight of the total composition:
    0.1–30% 3-hydroxybenzoic acid,
    1–65% oil, and
    1–50% of a structuring agent which is a wax.

20. The composition of claim 19 wherein the structuring agent is a silicone wax.

* * * * *